United States Patent [19]
Scott et al.

[11] Patent Number: 5,902,327
[45] Date of Patent: *May 11, 1999

[54] COMPRESSIBLE TANNING ASSEMBLY

[75] Inventors: Allen Willard Scott, Plainfield; Phillip Edward Shireman, Martinsville; Delisa Sheryl Jameson, Indianapolis, all of Ind.

[73] Assignee: Spectrum Products, Inc., Indianapolis, Ind.

[*] Notice: This patent issued on a continued prosecution application filed under 37 CFR 1.53(d), and is subject to the twenty year patent term provisions of 35 U.S.C. 154(a)(2).

[21] Appl. No.: 08/631,567

[22] Filed: Apr. 12, 1996

[51] Int. Cl.$^6$ .................................................. A61N 5/00
[52] U.S. Cl. ........................................... 607/90; 607/94
[58] Field of Search .................... 607/80, 88, 90, 607/91, 94; 362/220, 285, 427; 250/493.1, 494.1, 504 R

[56] References Cited

U.S. PATENT DOCUMENTS

| | | | |
|---|---|---|---|
| 2,570,514 | 10/1951 | Boltuch | 240/81 |
| 2,611,367 | 9/1952 | Harkenrider | 128/396 |
| 3,045,100 | 7/1962 | Mills | 219/34 |
| 3,459,935 | 8/1969 | Bruner | 240/52 |
| 3,495,364 | 2/1970 | DeBella | 52/121 |
| 3,867,948 | 2/1975 | Kallenborn | 128/395 |
| 4,450,507 | 5/1984 | Gordin | 362/61 |
| 4,494,177 | 1/1985 | Matthews | 362/402 |
| 4,600,980 | 7/1986 | Dahlgren | 362/395 |
| 4,624,259 | 11/1986 | Welt | 128/396 |
| 4,651,263 | 3/1987 | Hancock | 362/402 |
| 4,660,561 | 4/1987 | Nielsen | 128/376 |
| 4,740,707 | 4/1988 | Thaw | 250/494.1 |
| 4,918,319 | 4/1990 | Kruithof | 250/504 R |
| 5,088,014 | 2/1992 | Boughey | 362/132 |
| 5,176,438 | 1/1993 | Fisherman | 362/99 |

FOREIGN PATENT DOCUMENTS 2248922  4/1992  United Kingdom.

OTHER PUBLICATIONS

SunQuest® Assembly and User Guide, Model SQ3000, Spectrum Products, Inc. (P1255–1).
Technical Manual, Document TMB5030, Salsa 10; Salsa 12; rev. 9502, with attached photographs.

*Primary Examiner*—Beverly M. Flanagan
*Assistant Examiner*—Bryan K. Yarnell
*Attorney, Agent, or Firm*—Woodward, Emhardt, Naughton Moriarty & McNett

[57] ABSTRACT

An assembly for tanning in which a canopy containing both a source of fluorescent tanning lamps and electronic ballasts is attached to and able to rotate about the upper end of a pivoting arm. The lower end of the pivoting arm is inserted within and able to rotate about a leg of a base which is in the shape of a dog leg, the bend being in the plane of rotation of the pivoting arm. A counterbalancing member is attached to both the base and to the pivoting arm near the dog leg bend. The planes of rotation of both the pivoting arm and the counterbalancing member lie on the closed side of the "U" shape of the base. The pivoting arm may be rotated about its connection to the base, such that the entire assembly is placed in a compressed condition. In this compressed condition, a strap attached to either the canopy or pivoting arm can be attached to the base to maintain the assembly in the compressed condition during transport and storage.

5 Claims, 6 Drawing Sheets

COMPRESSIBLE TANNING ASSEMBLY

BACKGROUND OF THE INVENTION

1. Field of the Invention

This invention presents improvements to the methods of arranging and supporting tanning assemblies.

2. Description of the Prior Art

Many tanning canopies are supported on an arm that holds the canopy from above its center, with the arm supported by a vertical, telescoping member that attaches to a base. This type of canopy uses a lock to secure the canopy in the desired rotational position.

Fluorescent lamps are generally used for creation of the tanning radiant energy. Such lamps require ballasts to modify their electrical power and prevent excessive power consumption. Often these ballasts are mounted in the base. Because of this the center of gravity is low, causing the assembly to be stable when used, but requiring substantial wiring and manufacturing costs.

In at least one design, the sun tanning canopy is supported by a pivoting arm attached rotatably to both the canopy and base. The weight of the canopy and the arm is counterbalanced by a counterbalancing member attached to both the pivoting arm and the base. The attachment of the counterbalance to the pivoting arm is through a bracket attached to the side of the arm.

Bases used to support tanning canopies are often arranged in a "T" or "U" shape. In at least one design with a "T" shaped base, the electrical ballasts are located in a box arrangement on the base, which necessitates the use of electrical wiring up a telescoping arm to transmit power to the canopy for the fluorescent lamps. In another design with a pivoting arm and a "U" shaped base, the counterbalancing member is arranged such that, when viewed from above, it lies on the open side of the "U".

A tanning canopy supported on a pivoting arm may be compressed into a relatively flat position against the base. However, if the canopy is then tilted or lifted such that the base no longer supports a sufficient weight of the canopy, then the counterbalancing member may extend the base.

SUMMARY OF THE INVENTION

The present invention concerns a tanning assembly. One aspect of the invention concerns a pivoting arm which connects a canopy to a base. The pivoting arm incorporates a dog leg bend rotatably attached at one end to the base and rotatably attached at the other end to the canopy. The dog leg bend lies generally in the plane described by rotation of the pivoting arm about the base. There is also a counterbalancing member connected at one end near the dog leg bend of the pivoting arm and at the other end to the base.

Another aspect of the invention concerns a restraint. The tanning assembly can be compressed such that the canopy is brought close to the base. When the tanning assembly is in this compressed condition, a readily disengageable and re-engageable restraint may be used to couple the base to either the canopy or the pivoting arm.

Another aspect of this invention is the relationship of the pivoting arm and counterbalancing member to the base. In one configuration, the base consists of two legs generally opposite each other and connected by an interconnecting member. This base is generally arranged in the shape of the letter "U". The attachment points for the pivoting arm and counterbalancing member are arranged such that their planes of rotation are generally located along the same side of the "U" shape of the base as is the interconnecting member.

These and other features and advantages will be apparent from the following description of the drawings, the description of the invention, the claims, and the drawings.

DESCRIPTION OF THE PREFERRED EMBODIMENT

Figure 1:
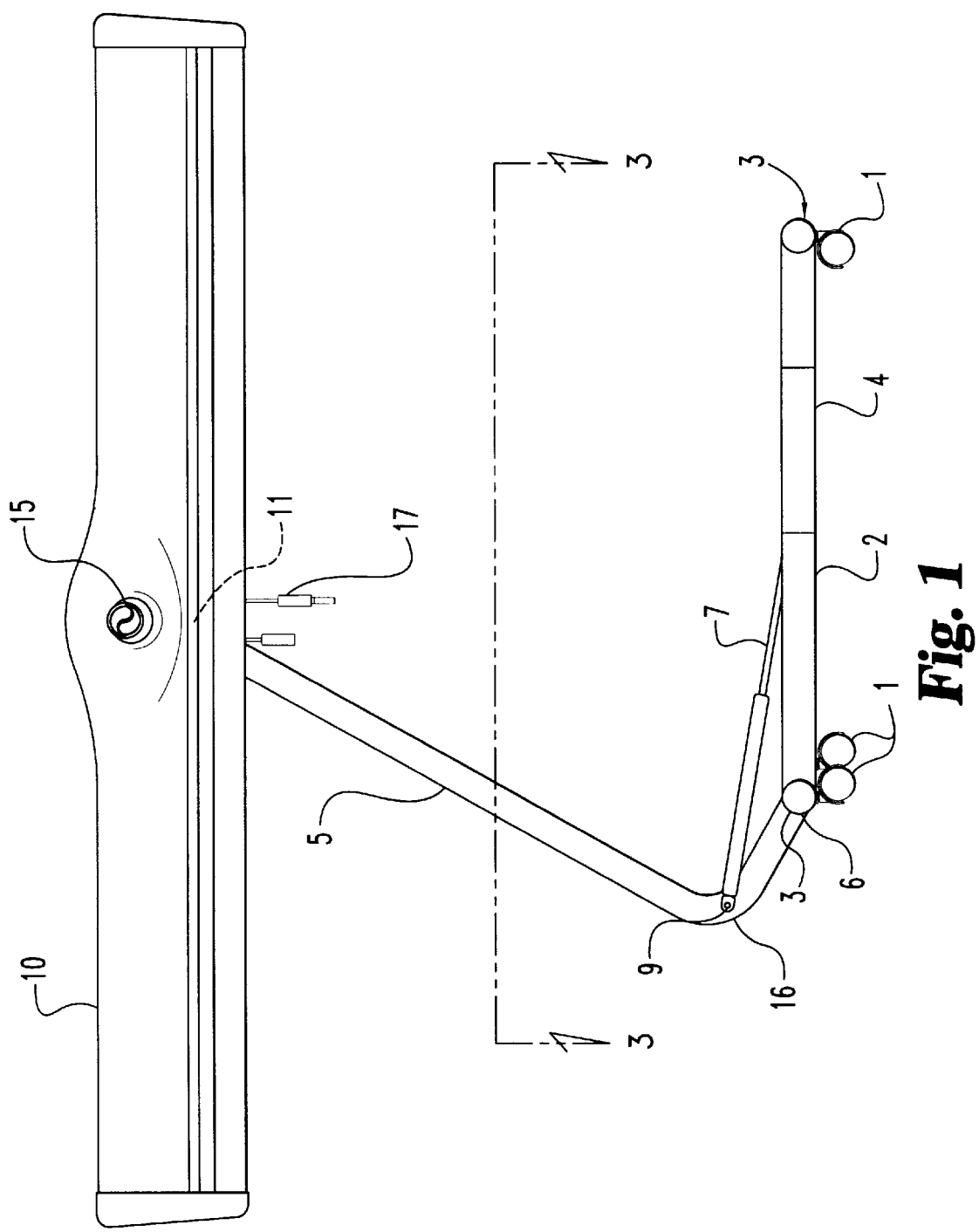
FIG. 1 is a side view of applicant's tanning assembly invention with the pivoting arm extended.

For the purposes of promoting an understanding of the principles of the invention, reference will now be made to the embodiment illustrated in the drawings and specific language will be used to describe the same. It will nevertheless be understood that no limitation of the scope of the invention is thereby intended, but rather the scope of the invention should be determined by the language of the claims, and equivalents thereto.

Referring to FIG. 1, applicant's tanning assembly invention has rollers 1 attached to the bottom of a base 2. This base consists of two opposite legs 3 connected by an interconnecting leg 4. Attached to this base is a pivoting arm 5. This pivoting arm 5 is connected to the base at a joint 6 that permits rotation. There is also a counterbalancing member 7, attached both to the base 2 at a joint 8 suitable for rotation, and also at a joint 9 suitable for rotation. Joint 9 is attached near the dog leg bend 16 of pivoting arm 5.

The pivoting arm 5 is also connected to a canopy 10. This connection occurs at a joint 11 suitable for rotation. This canopy 10 includes a timer 15 which may be used to adjust the time of exposure to the tanning energy.

Figure 2:
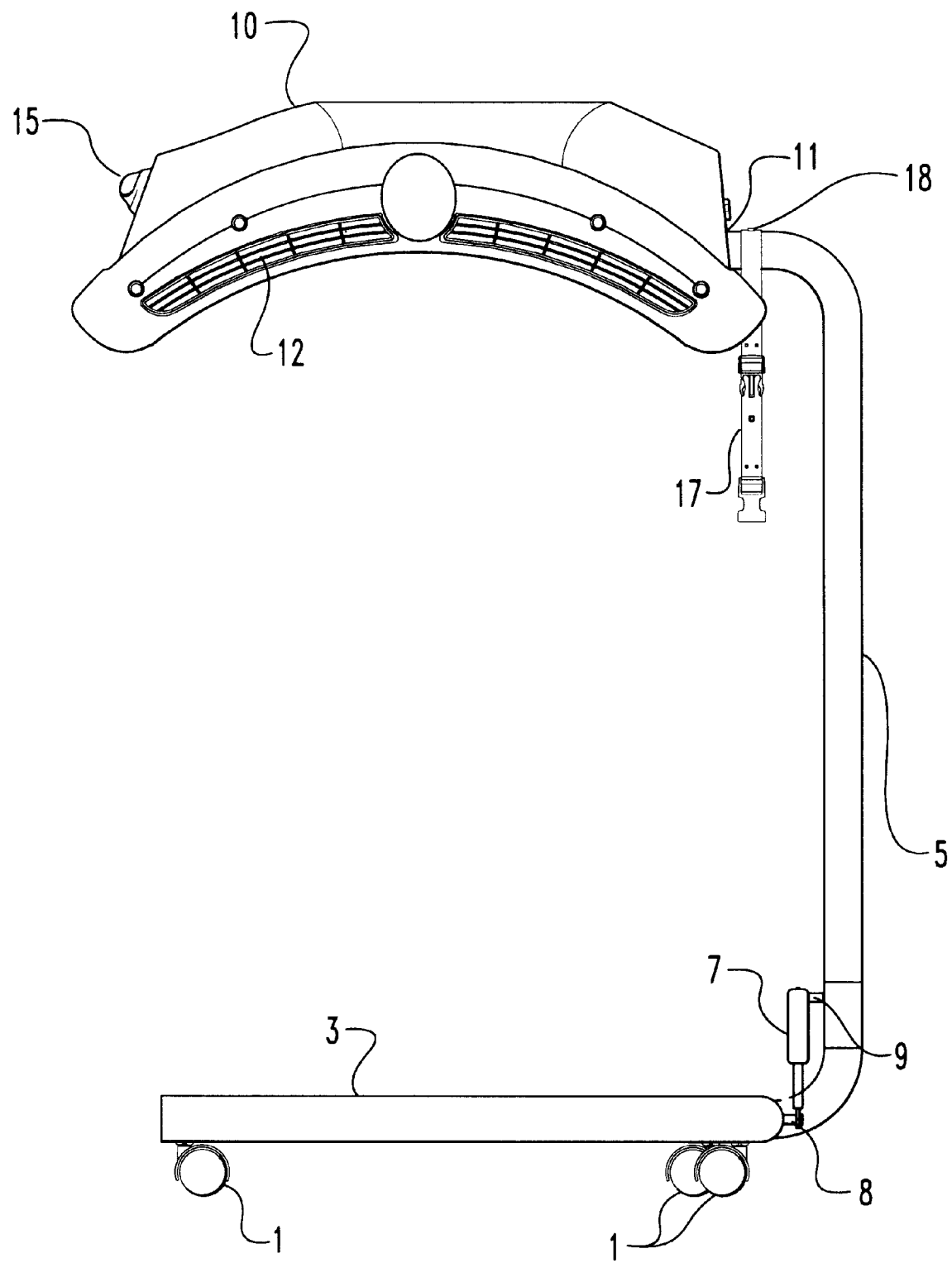
FIG. 2 is a side view of the tanning assembly of FIG. 1 with the pivoting arm extended.

Referring to FIG. 2, the canopy 10 includes ventilation slots 12 used to help keep the canopy cool.

Figure 6:
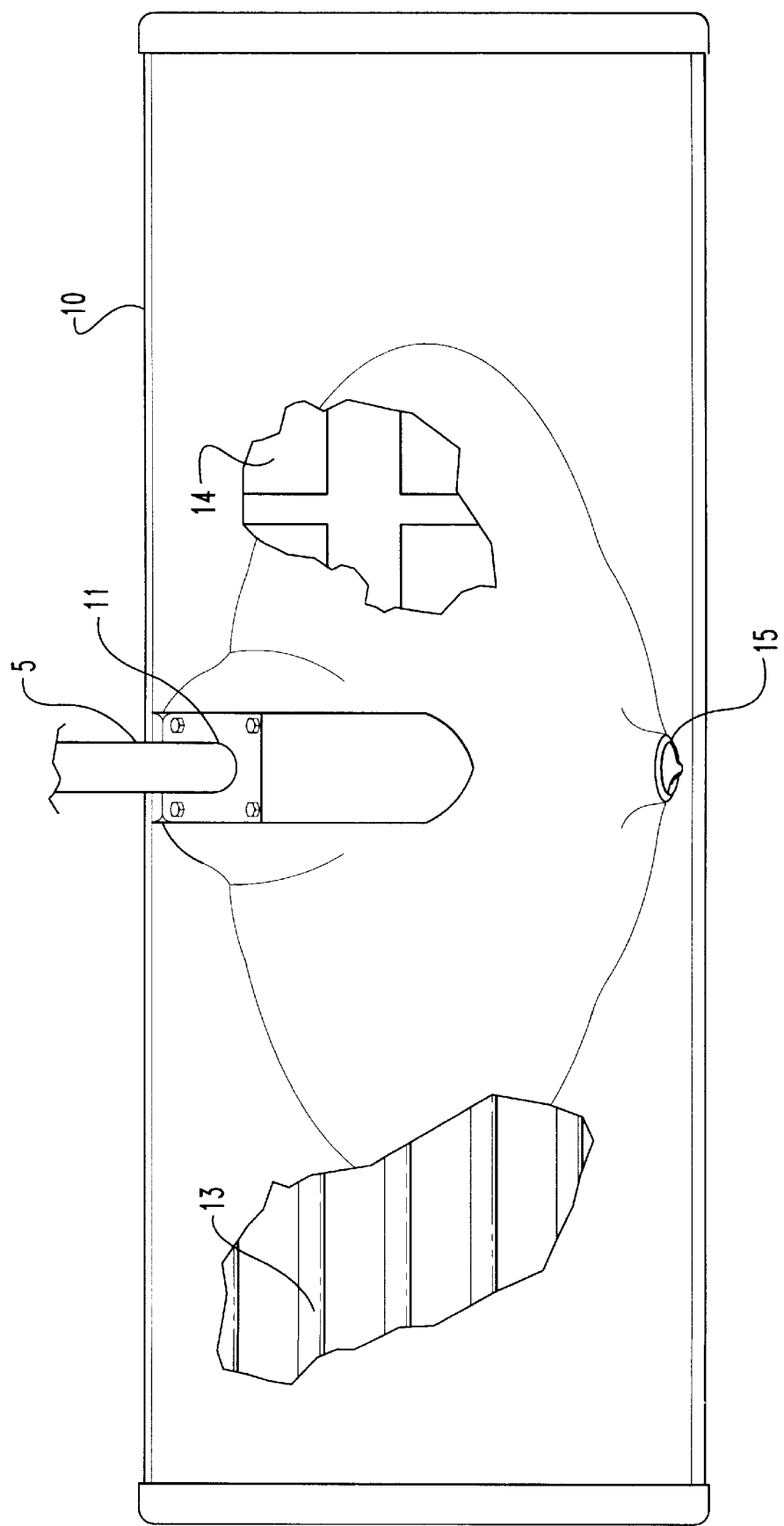
FIG. 6 is a view of the canopy of FIG. 1 from above with two sections removed.

FIG. 6 is a view of the canopy from above. The canopy includes one or more electronic ballasts 14. Also contained within the canopy 10 are the fluorescent lamps 13.

Figure 3:
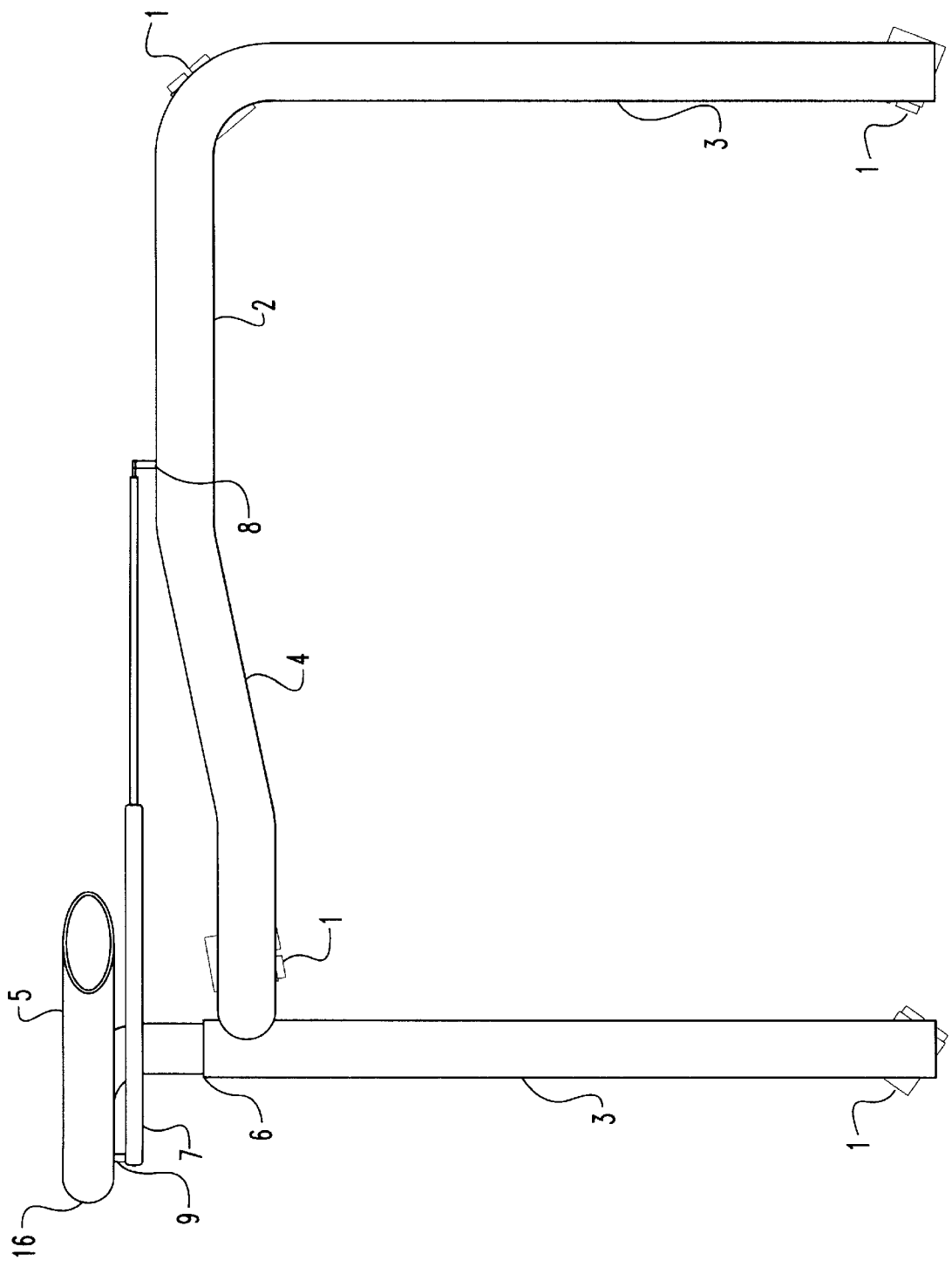
FIG. 3 is a sectional view of FIG. 1. The section is taken in a horizontal plane mid-way along the pivoting arm. The view looks upon the pivoting arm, counterbalancing member, base, and other features from above.

Refer to FIG. 3. FIG. 3 is a cross-sectional view taken approximately midway between the base and the canopy looking down upon the base. FIG. 3 shows the rollers 1 attached to the base 2. The base 2 consists of two, generally opposite legs 3, connected by an interconnecting member 4. As can be seen in FIG. 3, the general arrangement of the base is in the shape of the letter "U". The pivoting arm 5 is connected to the base 2 at a joint 6 that permits rotation. The counterbalancing member 7 is connected to the base 2 at a joint 8 that permits rotation. Vertical motion of the canopy 10 causes rotation of the pivot arm 5 about its joint to the base 6, and also rotation of the counterbalancing member 7 about its joint to the base 8. As can be seen in FIG. 3, these two planes of rotation lie generally on the same side of the "U" of the base as the interconnecting member 4.

Figure 4:
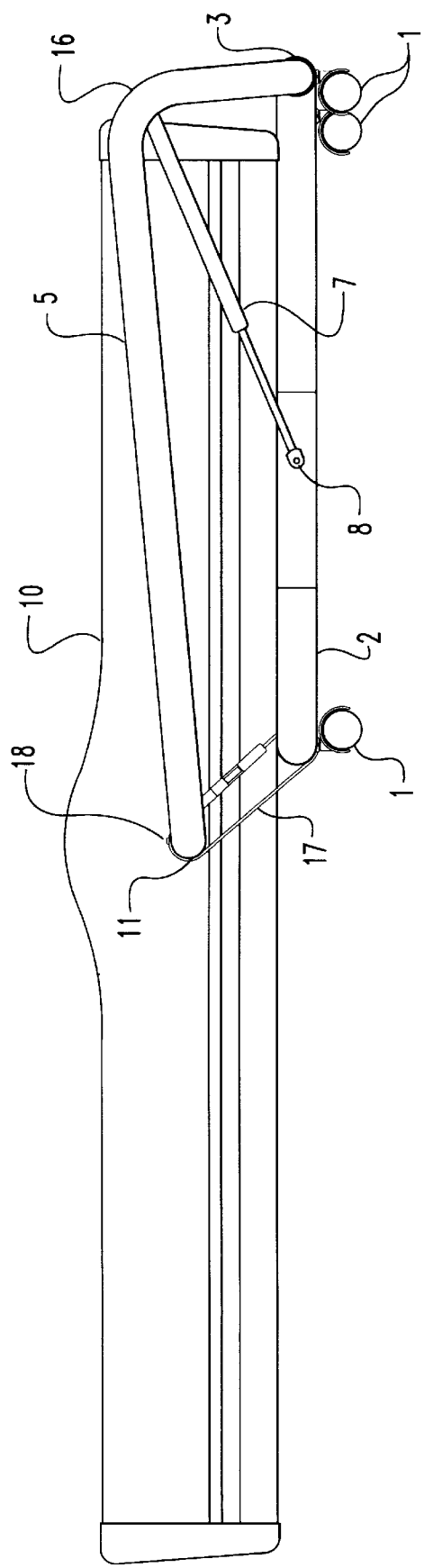
FIG. 4 is a side view of the tanning assembly of FIG. 1 in the compressed condition with the restraint engaged.
Figure 5:
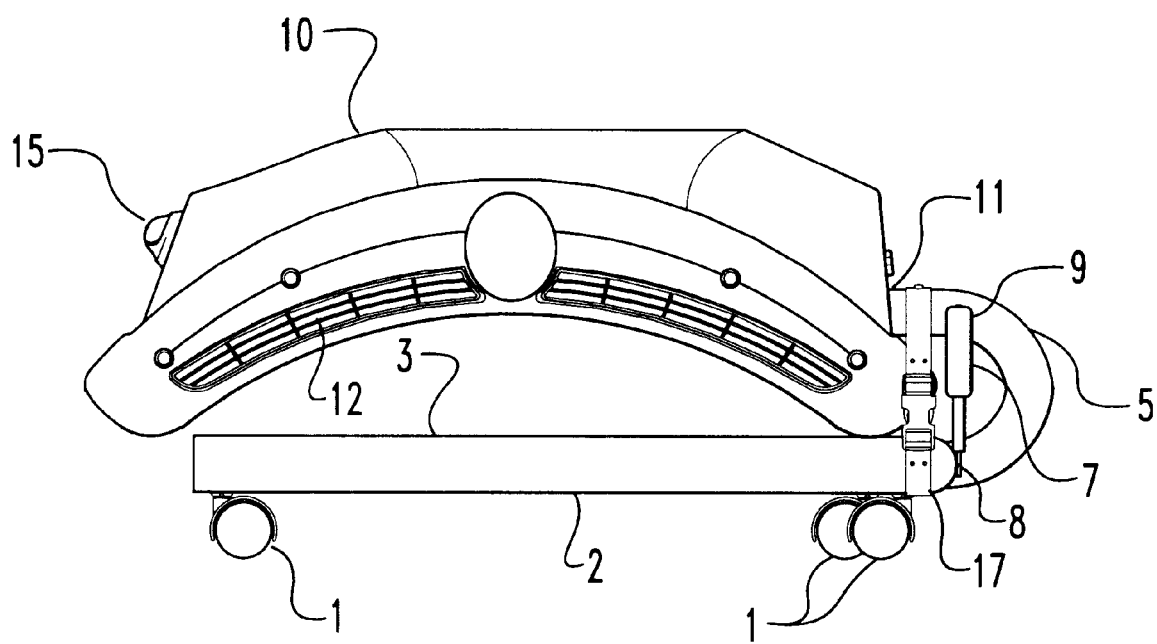
FIG. 5 is a view of the tanning assembly of FIG. 1 in the compressed condition with the restraint engaged.

FIGS. 4 and 5 show the tanning assembly in the compressed condition when the canopy 10 has been brought close to the base 2. In this compressed condition, a restraint 17 attached with a rivet 18 (or alternatively, a screw may be used) to the pivoting arm 5, is now engaged such that it also connects to the base 2.

What is claimed is:

1. A tanning assembly, comprising:

a canopy having a radiant energy source useful for tannin;

a base consisting of two legs generally opposite each other and connected by an interconnecting member, said base generally arranged in the shape of the letter U, said base incorporating a joint proximate the connection of a leg and the interconnecting member;

a pivoting arm having two ends, said pivoting arm being rotatably attached at one end to said canopy and at the other end rotatably attached to the joint of said base with the rotation of said pivoting arm about said base describing a plane that is generally located along the same side of the U-shape of said base as is the interconnecting member of said base, and a readily disengageable restraint, said restraint coupling said base to either said canopy or said pivoting arm.

2. The invention of claim 1, wherein said pivoting arm incorporates a dog leg bend rotatably attached at one end to the joint of said base and rotatably attached at the other end to said canopy with the dog leg bend lying generally in the plane described by rotation of said pivoting arm about said base; and said tanning assembly also includes a counterbalancing member connected at one end near the dog leg bend of said pivoting arm and at the other end to said base.

3. The invention of claim 2, wherein said restraint is attached to either said base, said canopy or said pivoting arm.

4. The invention of claim 3, wherein said canopy includes both one or more electronic ballasts which modify electrical power and provides the modified electrical power to one or more fluorescent lamps, and fluorescent lamps, which provide radiant energy useful for tanning; and said arm and said canopy can be readily and repeatedly adjusted to allow operation of said canopy in a horizontal position a plurality of distances from said base.

5. The invention of claim 4, wherein said canopy has an axis of rotation and a center of gravity, the axis of rotation of the attachment of said canopy to said pivoting arm is generally horizontal and generally intersecting the center of gravity of said canopy.

* * * * *

UNITED STATES PATENT AND TRADEMARK OFFICE
CERTIFICATE OF CORRECTION

PATENT NO : 5,902,327
DATED : May 11, 1999
INVENTOR(S) : Allen W. Scott; Phillip E. Sireman; and Delisa S. Jameson It is certified that error appears in the above-identified patent and that said Letters Patent are hereby corrected as shown below:

On the front page please delete "Woodward" under *Attorney, Agent or Firm* and insert in lieu thereof --Woodard--.
In column 1, line 38, please delete "ccmpressed" and insert in lieu thereof --compressed--.
In column 3, line 7, please delete "tannin" and insert in lieu thereof --tanning;--

Signed and Sealed this

Tenth Day of April, 2001

*Attest:*

NICHOLAS P. GODICI

*Attesting Officer*   *Acting Director of the United States Patent and Trademark Office*